(12) United States Patent
Hill et al.

(10) Patent No.: US 10,888,709 B2
(45) Date of Patent: Jan. 12, 2021

(54) MEDICAL APPARATUS AND METHOD

(71) Applicant: Polyphotonix Limited, Sedgefield, Durham (GB)

(72) Inventors: Duncan John Hill, Sedgefield (GB); Thomas Snell, Sedgefield (GB)

(73) Assignee: Polyphotonix Limited, Sedgefield, County Durham (GB)

( * ) Notice: Subject to any disclaimer, the term of this patent is extended or adjusted under 35 U.S.C. 154(b) by 0 days.

(21) Appl. No.: 14/916,863

(22) PCT Filed: Aug. 29, 2014

(86) PCT No.: PCT/GB2014/052627
§ 371 (c)(1),
(2) Date: Mar. 4, 2016

(87) PCT Pub. No.: WO2015/033114
PCT Pub. Date: Mar. 12, 2015

(65) Prior Publication Data
US 2016/0220841 A1 Aug. 4, 2016

(30) Foreign Application Priority Data

Sep. 5, 2013 (GB) .................................. 1315836.5

(51) Int. Cl.
*A61N 5/06* (2006.01)

(52) U.S. Cl.
CPC .... *A61N 5/0622* (2013.01); *A61N 2005/0627* (2013.01); *A61N 2005/0648* (2013.01); *A61N 2005/0652* (2013.01); *A61N 2005/0653* (2013.01); *A61N 2005/0656* (2013.01);
(Continued)

(58) Field of Classification Search
CPC ...... A61N 5/06–2005/073; A61B 18/20–18/28
See application file for complete search history.

(56) References Cited

U.S. PATENT DOCUMENTS

| | | | |
|---|---|---|---|
| 4,444,190 A * | 4/1984 | Mutzhas | A61N 5/0621 250/503.1 |
| 5,015,924 A | 5/1991 | Berman et al. | |
| 7,015,636 B2 | 3/2006 | Bolta | |

(Continued)

FOREIGN PATENT DOCUMENTS

| | | | |
|---|---|---|---|
| CH | 2019250 A1 * | 1/2009 | ............. F21S 8/086 |
| CN | 102439512 A | 5/2012 | |

(Continued)

OTHER PUBLICATIONS

Examination Report from the European Patent Office for corresponding European Application No. EP14 758 632.5, dated Apr. 7, 2017, 4 pages.

(Continued)

*Primary Examiner* — Jonathan T Kuo
(74) *Attorney, Agent, or Firm* — Klarquist Sparkman, LLP

(57) ABSTRACT

A medical apparatus and method of operating a medical apparatus are disclosed. The apparatus includes a radiation source for emitting electromagnetic radiation towards one or both eyes of a patient; wherein the apparatus is configured to emit electromagnetic radiation having a ratio of scotopic luminous intensity to photopic luminous intensity of at least 1.85:1.

10 Claims, 2 Drawing Sheets

(52) U.S. Cl.
CPC ............... *A61N 2005/0662* (2013.01); *A61N 2005/0667* (2013.01)

(56) References Cited

U.S. PATENT DOCUMENTS

| | | | |
|---|---|---|---|
| 2004/0093045 A1 | 5/2004 | Bolta | |
| 2004/0225340 A1 | 11/2004 | Evans | |
| 2005/0278003 A1 | 12/2005 | Feldman | |
| 2013/0060306 A1* | 3/2013 | Colbauch | A61N 5/0618 607/88 |
| 2014/0187998 A1* | 7/2014 | Lang | A61N 5/0622 600/558 |
| 2014/0257439 A1* | 9/2014 | Douglas | A61N 5/0618 607/90 |

FOREIGN PATENT DOCUMENTS

| | | |
|---|---|---|
| EP | 2019250 A1 | 1/2009 |
| WO | WO2011/141840 A1 | 11/2011 |
| WO | WO2012/123709 A1 | 9/2012 |

OTHER PUBLICATIONS

International Search Report and Written Opinion of the International Searching Authority, dated Oct. 29, 2014, for corresponding International Application No. PCT/GB2014/052627, 12 pages.

International Preliminary Report on Patentability and Written Opinion of the International Searching Authority, dated Mar. 17, 2016, for corresponding International Application No. PCT/GB2014/052627, 8 pages.

First Office Action and Search Report from the Patent Office of the People's Republic of China for corresponding Chinese Patent Application No. CN201480060273.3, dated Jun. 28, 2017, 15 pages.

Search Report (including English translation) from the National Intellectual Property Administration, People's Republic of China, for corresponding Chinese Patent Application No. 201480060273.3, dated Jan. 29, 2018, 6 pages.

Office Action (including English translation) from the Japan Patent Office, for Japanese Patent Application No. 2016-539631, dated May 29, 2018, 9 pages.

English translation of the Office Action from the Taiwan Patent and Trademark Office, for Taiwanese Patent Application No. 103130235, dated Jul. 20, 2018, 7 pages.

Examination Report from IP Australia, for Australian Patent Application No. 2014316860, dated May 31, 2018, 3 pages.

Arden et al., "A preliminary trial to determine whether prevention of dark adaption affects the course of early diabetic retinopathy," *Eye*, 24, pp. 1149-1155 (2010).

Chen et al., "Retinopathy of prematurity," *Angiogenesis*, 10:133-140 (2007).

Rao et al., "A direct and melanopsin-dependent fetal light response regulates mouse eye development," *Nature*, vol. 494, Feb. 14, 2013, pp. 243-247.

* cited by examiner

MEDICAL APPARATUS AND METHOD

CROSS REFERENCE TO RELATED APPLICATIONS

This is the U.S. National Stage of International Application No. PCT/GB2014/052627, filed Aug. 29, 2014, which in turn claims the benefit of and priority to United Kingdom Patent Application No. GB1315836.5, filed Sep. 5, 2013.

The present invention relates to a medical apparatus and method. In particular, but not exclusively, the present invention relates to a facial mask or other apparatus for directing radiation into a patient's eyes, and a method of operating such a medical apparatus.

Phototherapy has been used for various therapeutic and cosmetic purposes. It generally involves the use of specific wavelengths of light radiation being administered to a patient. Phototherapy may be used to treat chronic infections such as hepatitis (A, B or C), bacterial infections, wounds, precancer conditions, seasonal affective disorder (SAD), various dermatological and cosmetic purposes such as skin rejuvenation, and various eye diseases such as diabetic macular edema, retinopathy of prematurity, wet or dry age-related macular degeneration (AMD) and diabetic retinopathy, for example.

Diabetic retinopathy is a condition in which damage to the retina in the eye occurs and is caused by diabetes. More specifically, diabetic retinopathy is the result of microvascular retinal changes where hyperglycemia-induced intramural pericyte death and thickening of the basement membrane cause damage to the wall of blood vessels in the eye. This damage changes the formation of the blood-retinal barrier and also makes the retinal blood vessels become more permeable. Small blood vessels, such as those in the eye, are particularly vulnerable to poor blood sugar control. An overaccumulation of glucose and/or fructose damages the blood vessels in the retina. Damaged blood vessels are likely to leak fluid and lipids onto the macula.

Age-related macular degeneration (AMD) is a condition that affects the central vision of the eye. In the case of wet AMD, blood vessels begin to grow underneath the macula. These blood vessels often grow abnormally and ultimately lead to broken blood vessels and blood and protein leakage beneath the macula. Bleeding, leaking and scarring from these blood vessels eventually cause irreversible damage to the photoreceptors and therefore rapid loss of vision if left untreated.

Damaged blood vessels also result in reduced oxygen supply to the retina. This can cause over expression of vascular endothelial growth factor (VEGF). VEGF is part of a system that restores oxygen supply to tissues when the blood circulation is inadequate by stimulating vasculogenesis (new vessel formation) and angiogenesis (proliferation and migration of vessel cells). As such, new blood vessels are formed and these can then also be subject to damage as described above. Left untreated, diabetic retinopathy and wet AMD are therefore likely to continue to worsen and lead to impaired vision and ultimately blindness.

These conditions can be treated by preventing the complete dark adaptation of the eye by providing some degree of light radiation to the eyes or eyelids during sleep. This is because, during dark adaptation, the eye requires an increased oxygen level, and thus the blood vessels must work harder during dark adaptation. Therefore by preventing complete dark adaptation of the eye, the blood vessels are less stressed and can rejuvenate over time, and VEGF expression is reduced.

There are 3 known types of photoreceptor cells in the eye. Rods, cones and photosensitive retinal ganglion cells (pRGC), of which the cones can be further subdivided according to the particular opsin they contain (long (r), medium (g) and short (b) wavelength). Rods and cones are responsible for vision, and each type responds to a particular range of wavelengths, with rods being substantially more sensitive to low light levels than cones, but cones being better adapted to brighter light. Vision in low light levels where the rods are the dominant photoreceptor is known as Scotopic vision ($10^{-6}$-$10^{-2}$ cd/m$^2$), and the range of vision in which cones are primarily active is known as Photopic vision (1-106 cd/m$^2$). The borderline between the two is referred to as Mesopic vision ($10^{-2}$-1 cd/m$^2$). Colour is perceived by comparison between the response rates of different cell types. pRGCs are not involved in vision but are thought to be important in sleep cycles, melatonin generation and pupillary response.

It has been found useful to administer the radiation to the eye area by providing a mask type of device for a patient to wear during sleep, the mask configured to be secured over the patient's head to cover the eye area, and adapted to include light emitting sources in the region of the eyes. The light sources may be electroluminescent emitters, light emitting devices (LEDs), light emitting cells (LECs), light emitting electrochemical cells (LEECs), or organic light emitting devices (OLEDs), for example, and are arranged to emit light towards the eye area. The radiation acts to stimulate the rods of the eye leading to hyperpolarization and desensitization of the rod cells, which lowers their metabolic rates and hence results in a drop in oxygen consumption in the retina.

WO2011/135362, WO2012/025398 and WO2012/025399 disclose various radiation treatment apparatuses for directing electromagnetic radiation towards a patient.

Arden et al (Eye (2011) 25, 1546-1554) discloses a clinical study of patients with mild non-proliferative diabetic retinopathy or early, untreated non-sight-threatening diabetic macular oedema, wearing masks to illuminate the eyelid of one closed eye with 505 nm light. They concluded that sleeping in a dim light that can keep rods light adapted may reverse the changes of diabetic macular oedema, due to a decrease in dark-adaptation-associated oxygen consumption.

It would be useful to provide a medical apparatus that emits radiation with improved efficiency in terms of treating a patient's eye(s).

According to a first aspect of the present invention there is provided a medical apparatus comprising:
  a radiation source for emitting electromagnetic radiation towards one or both eyes of a patient;
  wherein the apparatus is configured to emit electromagnetic radiation having a ratio of scotopic luminous intensity to photopic luminous intensity of at least 1.85:1.

According to a second aspect of the present invention there is provided a method of manufacturing a medical device, comprising:
  providing a radiation source for emitting electromagnetic radiation towards one or both eyes of a patient;
  wherein the apparatus is configured to emit electromagnetic radiation having a ratio of scotopic luminous intensity to photopic luminous intensity of at least 1.85:1.

According to a third aspect of the present invention there is provided a method of treating a human patient with electromagnetic radiation, comprising:

directing electromagnetic radiation having a ratio of scotopic luminous intensity to photopic luminous intensity of at least 1.85:1 towards the eye or eyes of the patient.

Certain embodiments of the invention provide the advantage that an apparatus is provided that provides improved treatment efficiency compared to known devices.

Certain embodiments provide the advantage that the oxygen consumption of the eye may be reduced, thereby helping damaged blood vessels to be minimised or avoided in diabetic retinopathy or wet AMD patients.

Certain embodiments provide the advantage that disturbance of sleep during a treatment period may be reduced.

Embodiments of the invention are further described hereinafter with reference to the accompanying drawings, in which.

In the drawings like reference numerals refer to like parts.

The inventors have investigated the response of rods and cones in the eye to different wavelengths and intensities of light.

Rods and cones are the two main visual photoreceptor cells within the eye. Cones are primarily located around the centre of the field of vision, known as the yellow spot or the macula. The rods are mainly distributed around the areas of the retina outside of the macular. There are approximately 120 million rods in each eye and around 6 million cones.

During dark conditions there is no light to stimulate rods and cones. In such dark conditions the rod cells maintain a polarized state and continually release neurotransmitters. Maintenance of this polarized state is an energy consuming process. The retina therefore requires an increased supply of oxygen and sugars during dark conditions. If a patient already has damaged blood vessels in the eye, the increased oxygen and sugar supply is not helpful in preventing further damage, or in the repair of, existing blood vessels.

Upon absorption of light by a rod cell, a series of reactions shut the ion channels on the surface of the rod cell allowing the rod cell to become hyperpolarized and the release of neurotransmitters is suppressed. The oxygen and sugar demand from the retina is therefore lessened and the risk of damaged blood vessels is reduced.

It is this suppression of neurotransmitters upon absorption of light and subsequent reduction in damage to blood vessels that has led to investigations into to use of light emitting masks for sufferers of diabetic retinopathy and wet AMD to help prevent further damage to blood vessels, and possibly allow damaged blood vessels to repair.

Figure 1:
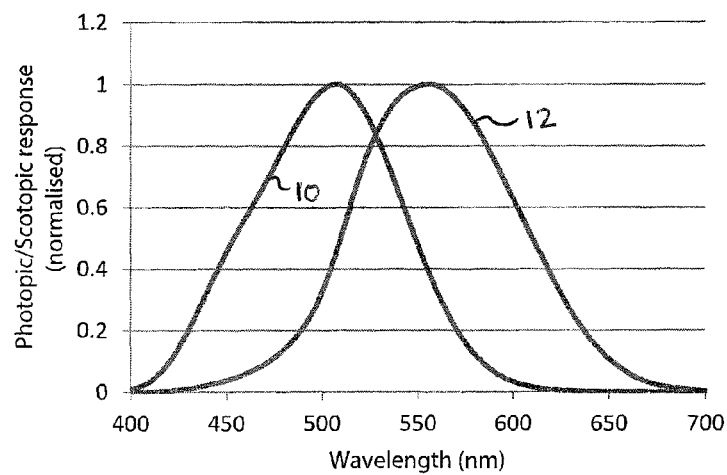
FIG. 1 illustrates the scotopic and photopic luminosity functions.

FIG. 1 illustrates the general response of rods and cones to light across a spectrum of wavelengths. In other words FIG. 1 illustrates the probability that a rod (curve 10) or cone (curve 12) will respond to the absorption of a photon of a particular wavelength by that cell. These curves are known in the art as the scotopic and photopic luminosity functions (curves 10 and 12 respectively). The rods are mainly responsive to light in the scotopic wavelength range (about 400 nm to 610 nm), and are most responsive to light at about 500 nm wavelength. Cones 12 (considered as a group including all three types of cones described above) are mainly responsive to light in the photopic wavelength range (about 475 nm to 650 nm), and are most responsive to light with a wavelength of about 575 nm.

The inventors have realised that the response of both the rods and the cones to a specific wavelength of light should be considered when devising a light emitting apparatus. The rods and cones have different probabilities of responding to incident light, and that response, if any, is different between rods and cones. For example, a rod is much more likely than a cone to respond to photon of 450 nm wavelength. A photon at 550 nm wavelength, however, is more likely to stimulate a cone than a rod.

In addition, the response of the rods and cones should be taken into consideration when measuring the brightness of light of relevance to the human eye, when devising a light emitting apparatus. The luminous intensity of light is measured in Candelas (Cd) and is defined as the power emitted by a light source in a particular direction weighted by the appropriate luminosity function (scotopic or photopic).

For example, to calculate the photopic luminous intensity of a light source having a specific wavelength, the radiant intensity of that light source is multiplied by the value of the photopic luminosity function at that wavelength and finally multiplied by an additional constant factor, 683.002. Similarly, to calculate the scotopic luminous intensity of a light source having a specific wavelength, the radiant intensity of that light source is multiplied by the value of the scotopic luminosity function at that wavelength and finally multiplied by an additional constant factor, 1700. The constant factors are required for historical reasons based on an 'old' definition of the Candela, which will be known to those skilled in the art, and will not be discussed in detail.

Generally, light sources are not monochromatic, and as such have a range of emission wavelengths. The emission spectrum of the light source can be defined as a function of wavelength $I_e(\lambda)$. To calculate the photopic luminous intensity, $I_p$, of such a light source, an integral over the range of wavelengths of the light source is required:

$$I_p = 683.002 \int_{\lambda_{min}}^{\lambda_{max}} y_p(\lambda) I_e(\lambda) d\lambda$$

where $y_p(\lambda)$ is the photopic luminosity function (curve 12 as shown in FIG. 1), and where $\lambda_{min}$ and $\lambda_{max}$ are the minimum and maximum wavelengths emitted by the light source.

Similarly, the scotopic luminous intensity, $I_s$, is calculated by:

$$I_s = 1700 \int_{\lambda_{min}}^{\lambda_{max}} y_s(\lambda) I_e(\lambda) d\lambda$$

where $y_s(\lambda)$ is the scotopic luminosity function (curve 10, as shown in FIG. 1).

Figure 2:
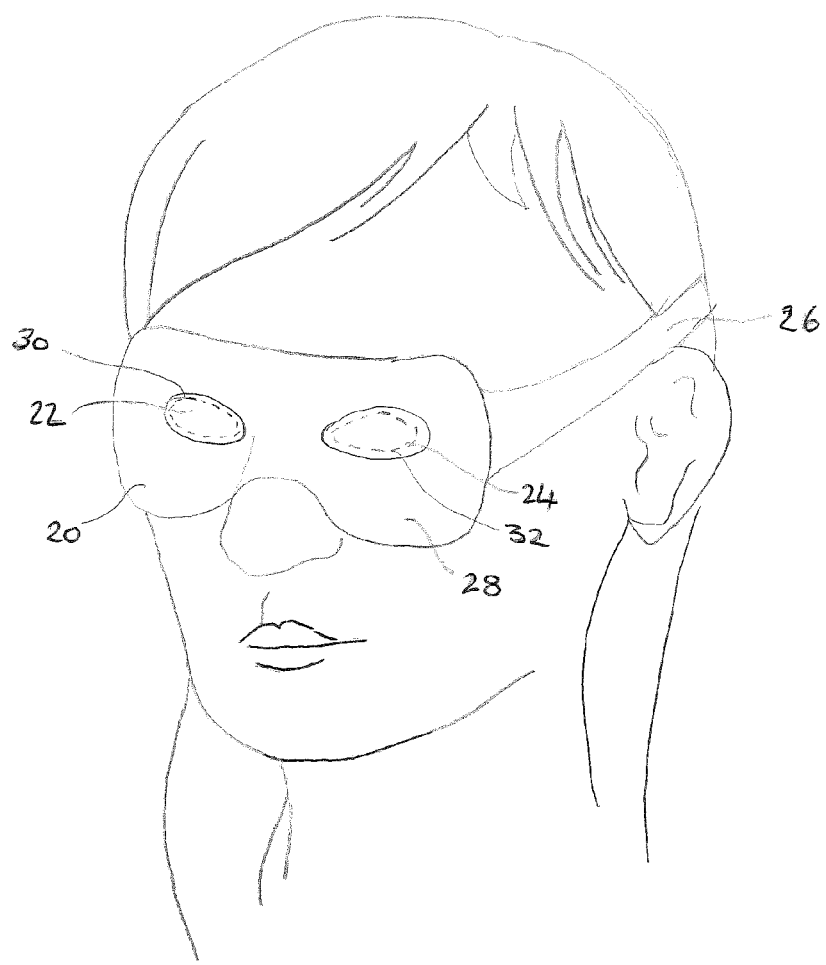
FIG. 2 illustrates a radiation treatment device.

For radiation treatment of the eye, a light source can be directed towards the eye of a patient. FIG. 2 illustrates an example of a radiation treatment apparatus, which is a facial mask 20 suitable for securing one or more light emitting source 30, 32 in position in use. The light emitting source may be an OLED array, for example. The facial mask 20 includes supporting regions 22, 24 to be located adjacent to the eyes of a patient, the supporting regions 22, 24 each supporting a respective light emitting source source. Of course, if only one eye is to be treated only one light source is required. The supporting regions 22, 24 are positioned to match the spacing between a patient's eyes. This spacing may be the average spacing between eyes, or 'tailor made' to fit the requirements of the particular patient, or the supports may be adjustable regions that are moveable between predetermined limits. A securing strap 26, secures the apparatus to the patient's head. The light sources are powered by at least one battery housed in or secured to the body 28 or the strap 26 of the mask. It will be appreciated that alternatively an external battery or power supply may also be used.

To effectively treat diabetic retinopathy and/or wet AMD, the light reaching the eye should have certain specific properties. The present inventors have found that providing a radiation treatment apparatus (for example as described above), in which light having a ratio $I_s:I_p$ of 1.85:1 is emitted provides an improved treatment efficiency and reduces the disturbance of sleep in the majority of patients compared to known devices. Aptly, $I_s:I_p$ of the light source is 2:1 or greater. Aptly, $I_s:I_p$ of the light source is 2.5:1 or greater. More aptly, $I_s:I_p$ of the light source is 3:1 or greater. More aptly, $I_s:I_p$ of the light source is 4:1 or greater. More aptly, $I_s:I_p$ of the light source is 5:1 or greater. More aptly, $I_s:I_p$ of the light source is 7.5:1 or greater. More aptly, $I_s:I_p$ of the light source is 10:1 or greater.

The inventors have found that it is advantageous to maximise the scoptopic luminous intensity of the light source and minimise the photopic luminous intensity of the light source. This is because, light in the scotopic range stimulates the rods, thereby reducing oxygen demand, reducing VEGF expression, and ultimately reducing the risk of damaged blood vessels and possibly allowing existing blood vessels to repair. Also, because damage to blood vessels in the eye occurs mainly during dark conditions when the patient is asleep, then radiation treatment should occur when the patient is asleep. Therefore, since light in the photopic range is likely to wake a patient, or disturb their sleep, this type of light should be minimised.

As such, the ratio of the scotopic luminous intensity and photopic luminous intensity, $I_s:I_p$, of the light source should be carefully considered.

Production of a device having an emission spectrum to satisfy the above-mentioned $I_s:I_p$ ratios can be achieved in a number of ways.

Various facial masks for emitting light radiation towards the eyes are known per se. These types of facial mask are provided with a radiation source for emitting electromagnetic radiation to the eye. To customise the light received by the eye, the radiation source itself can be devised accordingly, or a filter or other means may be used to modify the electromagnetic radiation prior to reaching the eye.

Electroluminescent devices, for example LEDs and OLEDs produce spectra that are related to the emission material and the optical properties of layers containing various emitting and charge transport materials.

Figure 4:
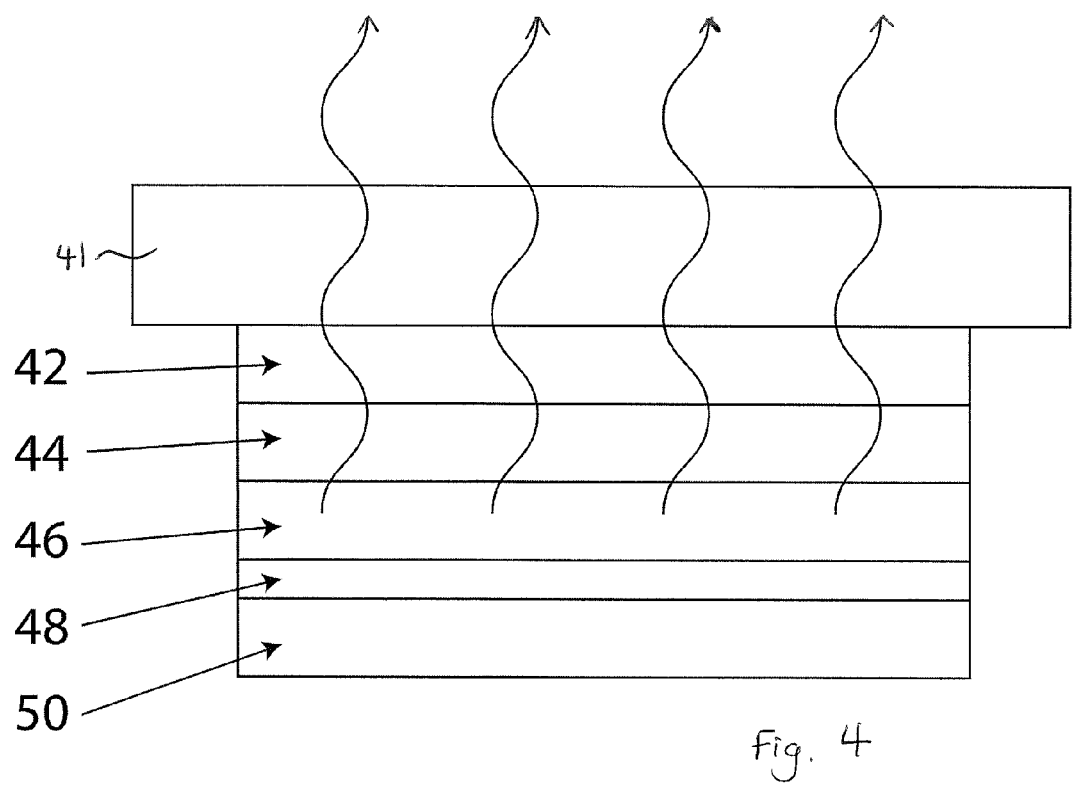
FIG. 4 illustrates an example of an OLED stack.

FIG. 4 illustrates an example of a light emitting source having a $I_s:I_p$ ratio around 1.85:1 suitable for use in a medical apparatus (where the $I_s$ value is more specifically around 1.83 to 1.87). The light emitting source is an OLED stack including: a first layer 42 of Indium Tin Oxide deposited onto a glass substrate 41, a second layer 44 of NPD (N,N'-Di-[(1-naphthyl)-N,N'-diphenyl]-1,1'-biphenyl)-4,4'-diamine) of thickness 160 nm; a third layer 46 of an 80:20 ratio of TPBi:Ir(ppy)3 (where TPBi is 1,3,5-Tris(1-phenyl-1H-benzimidazol-2-yl)benzene and Ir(ppy)3 is Tris[2-phenylpyridinato-C2,N]iridium(III)) having a thickness of 110 nm; a fourth layer 48 of LiF (lithium fluoride) having a thickness of 2 nm; and a fifth layer 50 of Al (aluminium) having a thickness of 100 nm. The stack is formed by vapour deposition of each layer in a manner known to those skilled in the art. When a voltage is applied, the light is emitted in the direction of the first layer, into the glass substrate 41 and beyond (as shown by the wavy arrows).

Of course it will be realised that other OLED stacks may be used, and the emitting materials may include fluorescent or phosphorescent materials. Additional layers, e.g. hole blocking, electron blocking and transport layers, may further be used to increase the efficiency of the device and/or tune the spectra of the radiation emitted.

A further example of a suitable polymer OLED is a solution processed device including: a first layer of a PEDOT:PSS (poly(3,4-ethylenedioxythiophene) poly(styrenesulfonate)) having a thickness of 60 nm (we note that the thickness of this layer may depend on the specific PEDOT type and so could be between 30 to 90 nm); a second layer of SPG-01T (which is a copolymer poly-spiro-bifluorene available from Merck) having a thickness of 80 nm; a third layer of LiF having a thickness of 2 nm; and an fourth layer of Al having a thickness of 100 nm. Such an OLED would have an $I_s:I_p$ ratio of 2.5:1 (where the $I_s$ value is more specifically around 2.48 to 2.52). In this case the method of depositing each layer in the stack was spin coating, though deposition methods of such solution processed devices may alternatively include gravure printing, slot die coating, wire bar coating, or aerosol/spray coating, for example.

A further example of a suitable polymer OLED is a solution processed device including: a first layer of Indium Tin Oxide deposited onto a glass substrate a second layer of a PEDOT:PSS (poly(3,4-ethylenedioxythiophene) poly(styrenesulfonate)) having a thickness of 60 nm (we note that the thickness of this layer may depend on the specific PEDOT type and so could be between 30 to 120 nm); a third layer of SPG-01T (which is a copolymer poly-spiro-bifluorene available from Merck) having a thickness of 80 nm; a fourth layer of LiF having a thickness of 2 nm; and a fifth layer of Al having a thickness of 100 nm. Such an OLED would have an $I_s:I_p$ ratio of 2.5:1 (where the $I_s$ value is more specifically around 2.48 to 2.52). In this case the method of depositing the PEDOT:PSS and SPG-01T layers in the stack was spin coating, though deposition methods of such solution processed devices may alternatively include gravure printing, slot die coating, wire bar coating, or aerosol/spray coating, for example. In this case the method of depositing the LiF and Al layers was thermal evaporation but it may also be by alternative deposition methods such as sputtering.

Alternatively an LED such as an Indium Gallium Nitride (InGaN) LED where the peak wavelength of the LED is controlled by the ratio between InN and GaN in the emissive layer may be used. Such an LED is grown on a substrate layer such as sapphire or silicon carbide using known epitaxy processes, and the ratio between InN and GaN controlled in this way. A wide range of peak wavelengths can be produced in this method from the near ultra violet (0.02InN/0.98GaN) through blues (0.3In/0.7Ga) through to reds for higher ratios. Such a device could be used to provide $I_s:I_p$ ratio of 4.5:1 (where the $I_s$ value is more specifically around 4.48 to 4.52).

Figure 3:
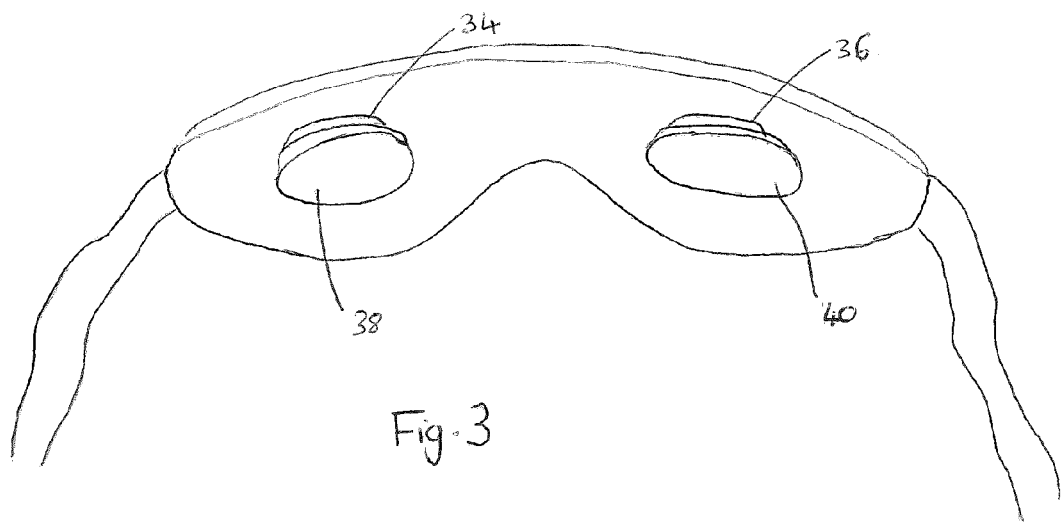
FIG. 3 illustrates further embodiment of a radiation treatment device.

In another example, a ratio, $I_s:I_p$ of 2:1 or greater may be obtained by using a generic device (eg. a known OLED, LED, electroluminescent source or fluorescent source), having an emission spectrum across a broad range of wavelengths, in combination with one or more optical filters. FIG. 3 illustrates an example of a radiation treatment apparatus (as described above) provided with generic OLED arrays 34, 36 in the eye regions, and optical filters 38, 40 located over the OLED arrays on the inner side of the apparatus (the eye facing side of the apparatus).

An example of a suitable notch filter would be a 500 nm notch filter which has a full width at half maximum of 10 nm. These filters are constructed through the evaporative deposition of materials with high and low refractive indices (for example $Ta_2O_5$ and $SiO_2$ respectively) and are commercially available. They may be used with any light source. Such a filter as described above would provide a resultant light having a ratio of 7.5:1 (where the $I_s$ value is more specifically around 7.48 to 7.52).

A further example of a notch filter centered at 492 nm with a full width at half maximum of 10 nm would provide a resultant light having a ratio of 10:1 (where the $I_s$ value is more specifically around 9.98 to 10.02).

The filter acts to filter the wavelengths of light that reach the eyes. A filter should block unwanted wavelengths of light, for example in the photopic range, and transmit required wavelengths, for example in the scotopic range. In this way the ratio $I_s:I_p$ can be changed to 2:1 or greater. Suitable filters include absorption filters (which absorb unwanted light), dichroic or interference filters (which reflect unwanted light), bandpass filters (which only transmit a certain wavelength band), longpass and shortpass filters (which transmit long and short wavelengths), monochromatic filters (only transmitting one wavelength) and guided-mode resonance filters. These filters are well known to those skilled in the art and will not be described in detail.

To demonstrate that a device is operating in the given range, the radiometric spectrum should be measured with a calibrated instrument capable of measuring radiometric spectra as a function of wavelength, such as a spectrometer or spectroradiometer. A full radiometric spectrum should be taken, and then the ratio calculated by application of the above-described formulae to the results.

Maximising the ratio, $I_s:I_p$, provides the additional advantage that the current draw of the device can be reduced compared to known models. OLEDs operate with relatively constant quantum efficiency meaning that the current draw is approximately proportional to the brightness or luminosity of the device. For example, a treatment device having a known generic OLED that gives a relatively low ratio, $I_s:I_p$ (e.g. 1:1), would require a higher current than a treatment device having an OLED having a relatively high ratio, $I_s:I_p$ (e.g. 3:1), for a patient to receive equal intensities of light suitable for stimulating the rods. Since a mask having an OLED with a higher ratio, $I_s:I_p$ requires a lower current draw, the battery life of the mask will be increased.

The treatment of conditions such as Diabetic Retinopathy and Wet Age Related Macular Degeneration, which place excessive strain on the oxygen levels in the retina, require the retina to be exposed to radiation for a set period, e.g. overnight. An advantage of the ratios of scotopic to photopic brightness as demonstrated above is that the oxygen consumption of the retina is reduced as far as possible without interrupting normal sleep patterns. The devices above also avoid significant quantities of light below 470 nm (aptly with less than 3% of the total light emitted less than 470 nm). Substantial accumulated exposure to light with wavelengths of 470 nm or less may result in damage to the eye. As a purpose of the apparatus is to treat the degeneration of the retina, a reduction in light levels below 470 nm is good.

Various modifications to the detailed designs as described above are possible. For example, point sources such as LEDs may be emitted into a waveguide, which can side-scatter light into the eye.

Although apparatus including a facial mask has been described above, it will be appreciated that other types of apparatus may be used to secure a light source in position, for example goggles, visors or glasses. Alternatively, the medical apparatus may include a stand or handle with a radiation source for emitting electromagnetic radiation towards one or both eyes of a patient disposed on it, to form a lamp or torch or similar object, to conveniently and comfortably direct light towards the patient.

Optionally the medical apparatus may contain a controller or other control mechanism, to control the dosage of radiation administered to the patient. The apparatus may include features such as a timer and/or sensors that detect when the patient is present or wearing the device. The dose may be administered such that the patient receives radiation for the entire sleeping period, or a period of, for example, between 1 hours and 8 hours within their overall sleeping period. Alternatively or in addition, the medical apparatus may have a user interface for enabling a patient or caregiver the capability to define the dosage period and/or dosage level, etc.

With the above-described arrangement the form factor of the facial mask is such that it can easily and comfortably be worn during sleep.

With the above-described arrangement the overall wavelength range and brightness of the total light for applying to a patient's eye(s) has been carefully tailored to suit the requirements of the retinal cells.

With the above-described arrangement an apparatus is provided that provides improved treatment efficiency compared to known devices.

Also, the oxygen consumption of the eye may be reduced, thereby helping damaged blood vessels to be minimised or avoided in diabetic retinopathy or wet AMD patients.

With the above-described arrangement the disturbance of sleep during a treatment period may be reduced.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of treating a human patient with electromagnetic radiation to reduce vascular endothelial growth factor expression for treating diabetic retinopathy or age related macular degeneration, the method comprising:
   directing electromagnetic radiation having a ratio of scotopic luminous intensity to photopic luminous intensity of at least 1.85:1 towards an eye or eyes of the patient; and
   wherein the electromagnetic radiation reaching the eye or eyes of the patient has a range of wavelengths and less than 3% of the total radiation has a wavelength less than 470 nm;
   thereby reducing vascular endothelial growth factor expression in the eye or eyes of the patient to treat diabetic retinopathy or age related macular degeneration.

2. The method of claim 1, further comprising selecting the human patient with the diabetic retinopathy for treatment.

3. The method of claim 1, further comprising selecting the human patient with the age related macular degeneration for treatment.

4. The method of claim 1, wherein the electromagnetic radiation is emitted from a radiation source comprising an OLED or LED.

5. The method of claim 1, wherein the electromagnetic radiation is emitted from a radiation source comprising fluorescent or phosphorescent material.

6. The method of claim 1, wherein the electromagnetic radiation is emitted from a radiation source mounted on a facial mask that is worn by the patient.

7. The method of claim 1, wherein the electromagnetic radiation is filtered by an optical filter to have the ratio of scotopic luminous intensity to photopic luminous intensity of at least 1.85:1.

8. The method of claim 1, wherein the ratio of scotopic luminous intensity to photopic luminous intensity is at least 2:1.

9. The method of claim 8, wherein the ratio of scotopic luminous intensity to photopic luminous intensity is at least 3:1.

10. The method of claim 9, wherein the ratio of scotopic luminous intensity to photopic luminous intensity is at least 5:1.

* * * * *